United States Patent
Kelly et al.

(10) Patent No.: US 9,346,731 B2
(45) Date of Patent: *May 24, 2016

(54) METHOD FOR PRODUCING LEVULINIC ACID FROM SLUDGE AND LIGNOCELLULOSIC BIOMASS

(71) Applicant: Georgia-Pacific LLC, Atlanta, GA (US)

(72) Inventors: John Patrick Kelly, Sugar Hill, GA (US); Michael Eugene Carroll, Loganville, GA (US); Paul Topping, Smyrna, GA (US)

(73) Assignee: Georgia-Pacific LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/487,193

(22) Filed: Sep. 16, 2014

(65) Prior Publication Data

US 2015/0080602 A1  Mar. 19, 2015

Related U.S. Application Data

(60) Provisional application No. 61/879,636, filed on Sep. 18, 2013.

(51) Int. Cl.
*C07C 51/00* (2006.01)
*C13K 13/00* (2006.01)

(52) U.S. Cl.
CPC .................. *C07C 51/00* (2013.01); *C13K 13/00* (2013.01); *Y02E 50/16* (2013.01)

(58) Field of Classification Search
None
See application file for complete search history.

(56) References Cited

U.S. PATENT DOCUMENTS

| 5,562,777 A | 10/1996 | Farone et al. |
| 6,054,611 A | 4/2000 | Farone et al. |
| 2015/0052806 A1 | 2/2015 | Frey et al. |
| 2015/0080603 A1* | 3/2015 | Kelly ..................... C07B 41/08 562/515 |

OTHER PUBLICATIONS

"Top Value Added Chemicals from Biomass: vol. I—Results of Screening for Potential Candidates from Sugars and Synthesis Gas"; Produced by Staff at the Pacific Northwest National Laboratory (PNNL) and the National Renewable Energy Laboratory (NREL); U.S. Department of Energy, Biomass Report; Aug. 2004.
"Levulinic Acid Production from Waste Biomass"; by Galletti et al.; BioResources 7(2), pp. 1824-1835; 2012.

* cited by examiner

*Primary Examiner* — Yevegeny Valenrod
(74) *Attorney, Agent, or Firm* — Ram W. Sabnis

(57) ABSTRACT

A method and integrated system for producing levulinic acid from the sludge of a pulp and paper mill and other lignocellulosic biomass is provided.

20 Claims, 2 Drawing Sheets

METHOD FOR PRODUCING LEVULINIC ACID FROM SLUDGE AND LIGNOCELLULOSIC BIOMASS

CROSS-REFERENCE TO RELATED APPLICATIONS

The present application claims benefit of U.S. Provisional Application No. 61/879,636, filed Sep. 18, 2013, the disclosure of which is incorporated herein by reference.

TECHNICAL FIELD

This invention relates to the production of levulinic acid from sludge and other lignocellulosic biomass.

BACKGROUND OF THE INVENTION

Pulp and paper manufacturers continually are looking for alternatives for use of waste produced during the manufacture of various paper-based products. Although some alternative disposal methods exist, there remains a need for cost effective methods to convert at least a portion of the sludge to one or more products having a higher value than use of the sludge as a combustible fuel or other commodity.

SUMMARY

Methods are provided for producing levulinic acid from a sludge and lignocellulosic biomass. Generally described, the methods comprise providing a sludge from a pulp and paper mill including one or more six carbon chain sugars; providing a lignocellulosic biomass; and converting the lignocellulosic biomass and sludge to levulinic acid in one or more reactors.

These and other features, aspects, and advantages of the present invention and embodiments thereof will become better understood when the following detailed description is read with reference to the accompanying drawing, where the components are not necessarily to scale and in which corresponding reference numerals designate corresponding parts throughout the drawings.

DETAILED DESCRIPTION OF EMBODIMENTS

Figure 1:
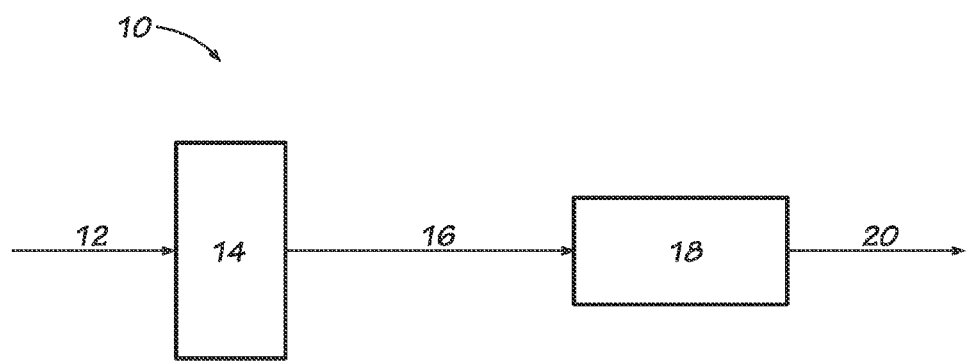
FIG. 1 is schematic diagram of an integrated reactor system for producing levulinic acid from sludge and lignocellulosic biomass according to an embodiment.

In the following description, numerous specific details are given to provide a thorough understanding of embodiments. The embodiments can be practiced without one or more specific details, or with other methods, components, materials, and the like. In other instances, well known structures, materials, or operations are not shown or described in detail to avoid obscuring aspects of the embodiments.

Reference throughout the specification to "one embodiment," "an embodiment," or "embodiments" means that a particular feature, structure, or characteristic described in connection with the embodiment is included in at least one embodiment. Thus, the appearances of the phases "in one embodiment" or "in an embodiment" in various places throughout the specification are not necessarily referring to the same embodiment. Furthermore, the particular features, structures, or characteristics may be combined in any suitable manner in one or more embodiments.

Methods and systems are provided for producing levulinic acid using the sludge from a pulp and paper mill and other lignocellulosic biomass. Integration of a system for converting sludge and lignocellulosic biomass to levulinic acid into an existing pulp and paper mill in accordance with embodiments of this disclosure may allow the production of levulinic acid with less capital investment and operating expense, and may provide operating cost savings in addition to producing a valuable product in levulinic acid.

Generally described, the methods include providing a sludge from a pulp and paper mill comprising one or more six carbon chain sugars; providing a lignocellulosic biomass; and converting the lignocellulosic biomass and sludge to levulinic acid in one or more reactors. In one embodiment, the step of converting the lignocellulosic biomass comprises at least partially hydrolyzing the lignocellulosic biomass to convert the one or more six carbon chain compound precursors to one or more six carbon chain sugars and, subsequently, converting the one or more six carbon chain sugars to levulinic acid. In one embodiment, the step of converting the sludge and lignocellulosic biomass to levulinic acid comprises also includes converting the sludge and lignocellulosic biomass to formic acid. For example, the step of converting the sludge and lignocellulosic biomass may produce both levulinic acid and formic acid.

The sludge and lignocellulosic biomass may be converted to levulinic acid in the same reactor or in separate reactors using either a continuous or batch process. In addition, the sludge may be added to the process streams or one or more reactors in a variety of locations. For example, in embodiments the sludge and lignocellulosic biomass may be mixed to form a biomass feed stream to a first reactor that at least partially hydrolyzes the lignocellulosic biomass and may partially convert the one or more six carbon chain sugars in the sludge to levulinic acid. In embodiments, the sludge and lignocellulosic biomass may be added separately to the first reactor. In embodiments, the lignocellulosic biomass may be partially hydrolyzed in the first reactor without the sludge, and the sludge may be combined with the partially hydrolyzed lignocellulosic biomass from the first reactor to form a partially hydrolyzed biomass feed stream for a second reactor to convert the one or more six carbon chain sugars in the partially hydrolyzed biomass feed stream to levulinic acid. In embodiments, the sludge and partially hydrolyzed lignocellulosic biomass may be added separately to the second reactor. In still other embodiments, the sludge and lignocellulosic biomass may be treated in reactors in parallel or in series.

The step of at least partially hydrolyzing the lignocellulosic biomass in the biomass feed stream may comprise contacting the lignocellulosic biomass with one or more of steam, at least one acid, or at least one alcohol. For example, in embodiments the step of at least partially hydrolyzing the lignocellulosic biomass in the biomass feed stream is performed at a temperature in the range of 150° C. to about 250° C., about 170° C. to about 240° C., about 170° C. to about 230° C., about 170° C. to about 220° C., or about 180° C. to about 210° C. In embodiments, the step of at least partially hydrolyzing the lignocellulosic biomass in the biomass feed stream may be carried out in a first reactor at a temperature of about 170° C. to about 190° C. for about 35 minutes to about 60 minutes. In embodiments, the first reactor is a tubular reactor with axial mixing, such as a continuous stirred-tank reactor (CSTR).

The conversion of the one or more six carbon chain sugars in the sludge may be carried out in the same reactor as the partial hydrolysis of the lignocellulosic biomass. The conversion of the one or more six carbon chain sugars to levulinic acid occurs very rapidly (on the order of seconds), while the hydrolysis of the lignocellulosic biomass requires a longer residence time (on the order of 30 to 60 minutes). In such embodiments the reactor system and operating conditions desirably are configured to maximize the conversion of the one or more six carbon chain sugars to levulinic acid while minimizing the degradation of any levulinic acid formed from the conversion of the sludge in the first reactor.

The conversion of the partially hydrolyzed lignocellulosic biomass may then be conducted in the same reactor or in a second reactor in series with the first reactor. The step of converting the one or more six carbon chain sugars generally is performed at a temperature in the range of about 150° C. to about 250° C. that is greater than the temperature used for partially hydrolyzing the lignocellulosic biomass. For example, in embodiments the step of converting the one or more six carbon chain sugars is conducted at a temperature of about 190° C. to about 220° C. for about 1 minute to about 15 minutes. While the step of converting the one or more six carbon chain sugars may be conducted in the same reactor as pre-hydrolysis, in embodiments the conversion is conducted in a second reactor comprising a tubular reactor with substantially no axial mixing, such as a plug flow reactor (PFR).

Sludge

As used herein, "sludge" refers to the residues that result from pulp and papermaking, and generally is recovered from wastewater streams of pulp and paper mills. The sludge may be a primary sludge, secondary sludge, recycle mill sludge, or blend of sludges, preferably obtained from pulp and paper mills. In embodiments, the sludge is an effluent stream from a pulp and paper mill, such as the whitewater stream of a pulp and paper mill. In embodiments, the sludge is recovered from the whitewater stream upstream of a primary clarifier in a pulp and paper mill or downstream of a primary clarifier and upstream of a secondary clarifier in a pulp and paper mill.

The composition of the sludge will vary depending on the raw material, process, and final product being manufactured. Generally, the sludge includes from 5 to 50% solids primarily including cellulose and other six carbon chain sugars. The solids content of the sludge optionally may be increased using one or more dewatering processes before the sludge is introduced into the integrated reactor systems described herein. For example, in embodiments the solids content of the sludge may be increased to about 20% prior to being diluted with acid before or after being added to the integrated reactor system.

Lignocellulosic Biomass

Suitable lignocellulosic biomass materials for producing levulinic acid generally include one or more six carbon chain compound precursors. The six carbon chain compound precursor or precursors can be converted to six carbon chain sugars. Desirably, the six carbon chain compound precursor or precursors are from the hemicellulose portion of a lignocellulosic biomass. Examples of suitable lignocellulosic biomass materials include any biological materials comprising lignocellulose that includes six carbon chain compound precursors, such as wood from trees, wood chips, slash or hog fuel from wood tree processing, forest residue, straw, chaff, grain, grasses, corn, corn husk, weeds, aquatic plants, and hay, and lignocellulose containing material of biological origin, such as some municipal waste or household waste.

Some lignocellulosic biomass materials have a higher six carbon chain sugar content for a greater yield of levulinic acid; therefore, selection of higher six carbon chain sugar content lignocellulosic biomass can result in higher levulinic acid yields and efficiency. For example, southern softwood includes a greater concentration of six carbon chain compounds in the hemicellulose portion than does hardwood. Therefore, southern softwood enables a higher yield of levulinic acid than does hardwood biomass.

If necessary, the particle size of the lignocellulosic biomass material can be reduced before introduction into the reaction system. Any manner known to be suitable to the skilled person can be used to reduce the particle size or otherwise increase the surface area of the lignocellulosic biomass material. Examples of such methods include crushing, grinding, milling, cutting, chipping, shredding, granulation, fibrillation, steam explosion, and any combination thereof.

Although not shown separately, the feed system can include a turpentine extractor to remove turpentine from wood biomass. The structure and operation of turpentine extractors are well known to those skilled in the art.

Reactor Systems

FIG. 1 is a schematic diagram of an embodiment of a reactor system 10 for producing levulinic acid from a sludge and lignocellulosic biomass. The system 10 includes a biomass feed stream 12 for introducing a lignocellulosic biomass and sludge to a first reactor 14. According to an embodiment, the first reactor 14 partially hydrolyzes the lignocellulosic biomass to form a first phase comprising partially hydrolyzed lignocelluosic biomass comprising cellulose and lignin and a second phase comprising one or more five carbon chain sugars and one or more six carbon chain sugars from degradation of hemicellulose in the lignocellulosic biomass. Additionally, the first reactor 14 converts at least a portion of the sludge to levulinic acid.

According to an embodiment, the hydrolyzing of the biomass feed stream may comprise contacting the biomass feed stream in the first reactor with one or more of steam, at least one acid, or at least one alcohol. Suitable acids include mineral acids such as hydrochloric acid, nitric acid, phosphoric acid, sulfuric acid, and the like, and organic acids such as acetic acid, formic acid, and the like. According to embodiments, the acid may be added to the biomass feed stream in an amount from about 0 to about 10% by weight of the biomass feed stream. According to an embodiment, the acid may be formed from a precursor, such as sulfur dioxide, added to the biomass feed stream. Suitable alcohols include methanol, ethanol, propanol, butanol, and the like.

The reaction parameters for the hydrolysis in the first reactor can be set to favor the production of the one or more five and six carbon chain sugars from the lignocellulosic biomass as opposed to a higher order reaction conversion such as to tar or char while also reducing the degradation of any levulinic acid that is formed. In accordance with an embodiment, the hydrolysis in the first reactor is conducted at a temperature of about 150° C. to about 250° C., about 170° C. to about 195° C., or about 170° C. to about 185° C. for a residence time of about 35 minutes to about 60 minutes or about 35 to 45 minutes.

The first reactor can be any type of reactor known to be suitable to those skilled in the art and optionally may include a pre-steaming device that receives the biomass feed stream and steam to heat the lignocellulosic biomass and sludge and begin the hydrolysis. The steam heated biomass feed stream is fed to or near the top of a vertical tube reactor. More steam and optionally acid or alcohol, as described hereinabove, is added to the biomass feed stream in the vertical tube reactor and the biomass is hydrolyzed as it passes from the top to the bottom of the reactor.

The first phase produced by hydrolysis in the first reactor is substantially solid and the second phase is substantially liquid and includes a solvent such as water or alcohol or both and any acid or alcohol used in the hydrolysis. This mixture of the first phase and the second phase optionally may be fed to a separator which separates the first phase from the second phase. The separator can be of a type known to those skilled in the art to be suitable for this purpose, non-limiting examples of which include a screw press, a belt press, a drum filter, a disc filter, or a centrifuge, or the like. Alternatively, the first and second phases may be introduced into a second reactor for further hydrolysis and conversion of the partially hydrolyzed lignocellulosic biomass into levulinic acid.

In an embodiment, the first phase comprising the partially hydrolyzed lignocelluosic biomass, which includes cellulose and lignin, may be delivered to a wood pulp product production system (described more herein below) or introduced into a second reactor for further hydrolysis. According to an embodiment, the second phase from the separator optionally may be fed to a different separator in which the solvent and acid are separated from the second phase by liquid-liquid extraction and returned as recycled solvent and acid to the first reactor.

The partially hydrolyzed lignocellulosic biomass, particularly the five and six carbon chain sugars, then may be fed from the first reactor, or optionally from the separator, to a second reactor and optionally one or more subsequent reactors for converting at least a portion of the one or more five carbon chain sugars and one or more six carbon chain sugars from the second phase into furfural, a furfural reaction intermediate, levulinic acid, tar, or a combination thereof. The reaction products then may be separated using methods known in the art.

In embodiments, the second reactor can be any reactor suitable to one skilled in the art for this purpose, non-limiting examples of which include an autoclave, a PFR, a batch reactor, or a CSTR. According to an embodiment, the second reactor is operated at a relatively low temperature and has a relatively low residence time. The reaction parameters of the second reactor can be set to favor the conversion of the one or more six carbon chain sugars from the second phase primarily to levulinic acid, and to avoid conversion of the one or more five carbon chain sugars from the second phase. For example, in embodiments the step of converting at least a portion of the one or more six carbon chain sugars is carried out in the second reactor at a temperature of about in the conversion reaction system is carried out at a temperature of about 150° C. to about 250° C., about 180° C. to about 230° C., or about 200° C. to about 210° C. at a pressure high enough so that the reactor contents do not reach their boiling point, such as about 10 psi above the vapor pressure of the liquid in the reactor, for a residence time of about 1 minute to about 15 minutes.

According to an embodiment, an acid such as a mineral acid or organic acid is added to the second reactor to convert the partially hydrolyzed lignocellulosic biomass to levulinic acid. Suitable mineral acids include hydrochloric acid, nitric acid, sulfuric acid, phosphoric acid, and the like, and suitable organic acids include, acetic acid, formic acid, and the like, and may be added to the partially hydrolyzed lignocellulosic biomass in the second reactor in an amount of from about 0 to about 10% by weight of the reactor contents or more depending on parameters such as the type of biomass, the particular acid, the temperature in the reactor and the like.

According to an embodiment, the resulting product stream, which may be a mixture of levulinic acid, furfural, and tar, may be transferred to a separator for the removal of levulinic acid. Any suitable separation system known to those skilled in the art can be used to separate the levulinic acid from the resulting product stream. According to embodiments, methods of levulinic acid separation include those such as liquid-liquid extraction, gas stripping, steam stripping, distillation and the like. The levulinic acid can then be captured in a condenser, purified in a purifier, and stored in a storage container.

According to an embodiment, a mixture of the levulinic acid and solvent and any acid used in the second reactor may be fed from the second reactor to a liquid-liquid extraction system for separating the levulinic acid from the solvent and acid. According to embodiments of this disclosure, other methods of levulinic acid separation include those such as gas stripping, steam stripping, distillation, and the like. The levulinic acid can then be stored in a levulinic acid storage container. The solvent and acid can be recovered and recycled via conduit for use in other operations. In some embodiments, the mixture fed to the extraction distillation system may include other residual substances which may also be separated and stored in a residual substance container. Such residual substance can also be used as a combustion fuel to produce heat.

Levulinic acid is useful in synthesis of polymers, pharmaceuticals, and chemical commodities such as methyltetrahydrofuran, valerolactone, and ethyl levulinate. Levulinic acid is also a photosensitizer for photodynamic therapy.

Alternatively, according to the embodiment illustrated in FIG. 1, the product stream 16 of the first reactor, including the first and second phases, can be fed from the first reactor 14 to a second reactor 18 for conversion of six carbon chain sugars or sugar precursors in the partially hydrolyzed lignocelluosic biomass to produce levulinic acid and formic acid 20.

Integration of the above-described method for producing levulinic acid from sludge and lignocellulosic biomass in a pulp and paper mill provides several advantages. For example, in such a process the amount of waste streams requiring disposal by landfill or other less economically beneficial means may be decreased while the production of a higher value product, such as levulinic acid, may increase the profitability of the overall process.

Figure 2:
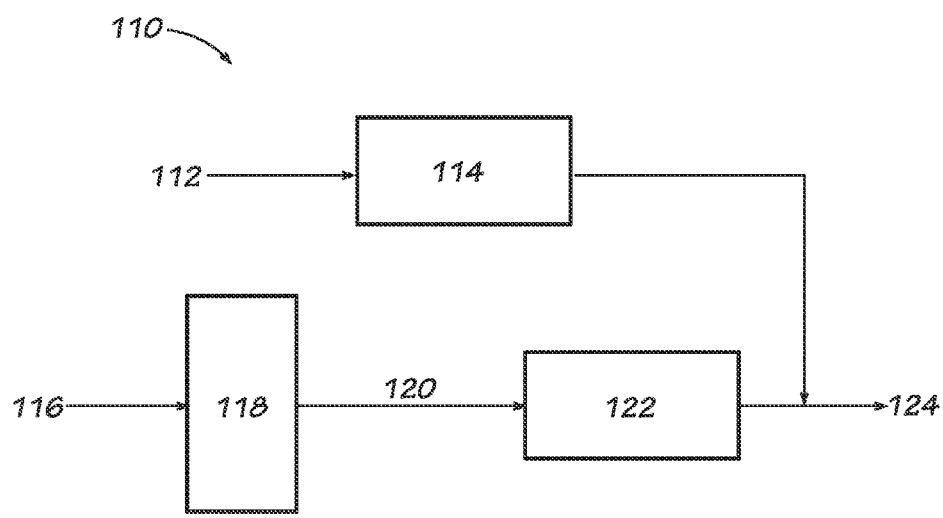
FIG. 2 is schematic diagram of an integrated reactor system for producing levulinic acid from sludge and lignocellulosic biomass according to an embodiment.

According to another embodiment illustrated in the schematic of FIG. 2, the reactor system includes one or more reactors for converting the sludge to levulinic acid in parallel with one or more reactors for converting the lignocellulosic biomass to levulinic acid. For example, the reactor system 110 may include a sludge reactor 114 for converting a sludge feed stream 112 to levulinic acid 124 in parallel with a first reactor 118 to partially hydrolyze a lignocellulosic biomass feed stream 116 to form a partially hydrolyzed lignocellulosic biomass stream 120, and a second reactor 122 to convert the partially hydrolyzed lignocellulosic biomass stream 120 to levulinic acid 124.

Figure 3:
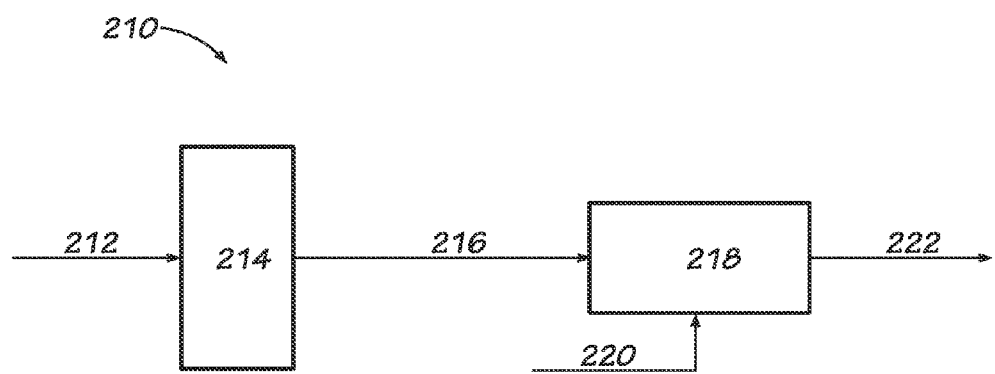
FIG. 3 is schematic diagram of an integrated reactor system for producing levulinic acid from sludge and lignocellulosic biomass according to an embodiment.

In still another embodiment illustrated in the schematic of FIG. 3, the reactor system 210 includes a first reactor 214 for partially hydrolyzing the lignocellulosic biomass feed stream 212 to form a partially hydrolyzed lignocellulosic biomass stream 216 that is subsequently introduced into a second reactor 218. The sludge 220 may be separately introduced into the second reactor 218, where both the partially hydrolyzed lignocellulosic biomass stream 216 and sludge 220 are converted into levulinic acid 222.

Figure 4:
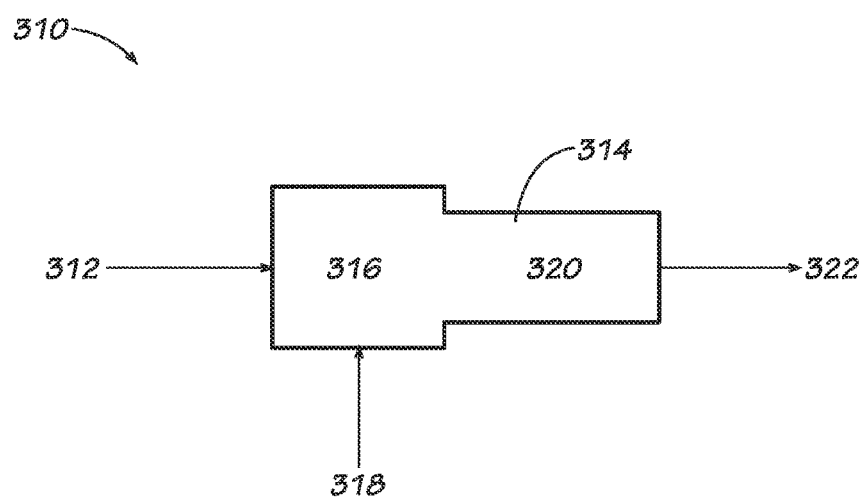
FIG. 4 is schematic diagram of an integrated reactor system for producing levulinic acid from sludge and lignocellulosic biomass according to an embodiment.

In still another embodiment illustrated in the schematic of FIG. 4, the reactor system 310 includes a reactor 314 for partially hydrolyzing a lignocellulosic biomass feed stream 312 in a first zone 316. A separate, sludge feed stream 318 may introduce the sludge into the first zone 316 (as illustrated) or downstream of the first zone in a second zone 320 (not shown), where the conversion of the partially hydrolyzed lignocellulosic biomass to levulinic acid 322 occurs.

In each of the above configurations, it should be noted that the reaction time for conversion of the sludge into levulinic acid is significantly less than that required for conversion of other lignocellulosic biomass, such as wood chips, into levulinic acid. Because of the disparity of reaction times, the reactor configuration and operating conditions should be optimized to increase conversion of the lignocellulosic biomass to one or more six carbon sugar chains without degrading any levulinic acid that is formed from the conversion of sludge in embodiments in which the biomass of the reactor includes both a lignocellulosic biomass and sludge. In such embodiments it can be advantageous to utilize a larger reactor that is operated at a lower temperature (i.e., such as a CSTR) as a first reactor followed by a smaller reactor that is operated at a higher temperature (i.e., such as a PFR).

It should be apparent that the foregoing relates only to embodiments of the present invention and that numerous changes and modifications can be made herein without departing from the scope of the invention as defined by the following claims and equivalents thereof.

We claim:

1. A method for producing levulinic acid, comprising:
    combining a sludge from a pulp and paper mill and a lignocellulosic biomass to produce a mixture comprising the sludge and the lignocellulosic biomass, wherein the sludge comprises one or more six carbon chain sugars, and wherein the lignocellulosic biomass comprises one or more six carbon chain sugar precursors; and
    converting the mixture comprising the sludge and the lignocellulosic biomass to a mixture comprising levulinic acid and tar in one or more reactors.

2. The method of claim 1, wherein the sludge and the lignocellulosic biomass are converted to the levulinic acid in separate reactors.

3. The method of claim 1, wherein the sludge and the lignocellulosic biomass are converted to the levulinic acid in the same reactor.

4. The method of claim 3, wherein the sludge and the lignocellulosic biomass are mixed together prior to being added to the reactor.

5. The method of claim 3, wherein the sludge and the lignocellulosic biomass are added separately to the reactor.

6. The method of claim 1, wherein converting the mixture comprising the sludge and the lignocellulosic biomass comprises:
    partially hydrolyzing the lignocellulosic biomass to form one or more additional six carbon chain sugars from the one or more six carbon chain sugar precursors; and
    converting the one or more six carbon chain sugars and the one or more additional six carbon chain sugars to the levulinic acid.

7. The method of claim 6, wherein partially hydrolyzing the lignocellulosic biomass comprises contacting the lignocellulosic biomass with steam, a mineral acid, an alcohol, or any combination thereof.

8. The method of claim 6, wherein the lignocellulosic biomass is partially hydrolyzed in a first reactor at a temperature of about 170° C. to 185° C. for about 35 minutes to about 60 minutes.

9. The method of claim 8, wherein the first reactor comprises a tubular reactor with axial mixing.

10. The method of claim 8, wherein the one or more six carbon chain sugars and the one or more additional six carbon chain sugars in the partially hydrolyzed mixture are converted to the mixture comprising the levulinic acid and the tar in a second reactor at a temperature of 190° C. to about 220° C. for about 1 minute to about 15 minutes.

11. The method of claim 10, wherein the second reactor comprises a tubular reactor with substantially no axial mixing.

12. The method of claim 1, wherein the sludge is provided from a whitewater stream upstream of a primary clarifier in the pulp and paper mill.

13. The method of claim 1, wherein the sludge is provided from a whitewater stream downstream of a primary clarifier and upstream of a secondary clarifier in the pulp and paper mill.

14. A method for producing levulinic acid, comprising:
    combining a sludge and a lignocellulosic biomass to produce a biomass feed, wherein the sludge is from a pulp and paper mill and comprises one or more six carbon chain sugars, and wherein the lignocellulosic biomass comprises one or more six carbon chain sugar precursors;
    partially hydrolyzing the biomass feed to produce a partially hydrolyzed biomass, wherein the one or more six carbon chain sugar precursors are hydrolyzed to produce one or more additional six carbon chain sugars;
    converting the one or more six carbon chain sugars and the one or more additional six carbon chain sugars to a mixture comprising levulinic acid and tar; and
    separating the levulinic acid from the tar to produce a levulinic acid product.

15. The method of claim 14, wherein the biomass feed is partially hydrolyzed to produce the partially hydrolyzed biomass at a temperature of about 170° C. to 185° C.

16. The method of claim 14, wherein the one or more six carbon chain sugars and the one or more additional six carbon chain sugars are converted to the mixture comprising the levulinic acid and the tar at a temperature of 190° C. to about 220° C.

17. The method of claim 14, wherein partially hydrolyzing the biomass feed comprises contacting the biomass feed with steam, a mineral acid, an alcohol, or any combination thereof to produce the partially hydrolyzed biomass.

18. The method of claim 17, wherein the biomass feed is contacted with the mineral acid, and wherein the mineral acid is present in an amount of up to 10% by weight of the biomass feed.

19. A method for producing levulinic acid, comprising:
    combining a sludge and a lignocellulosic biomass to produce a biomass feed, wherein the sludge is from a pulp and paper mill and comprises one or more six carbon chain sugars, and wherein the lignocellulosic biomass comprises one or more six carbon chain sugar precursors;
    partially hydrolyzing the biomass feed to produce a partially hydrolyzed biomass in a first reactor, wherein the one or more six carbon chain sugar precursors are hydrolyzed to produce one or more additional six carbon chain sugars;
    converting the one or more six carbon chain sugars and the one or more additional six carbon chain sugars to a mixture comprising levulinic acid and tar in a second reactor;

transferring a phase comprising a mineral acid, a solvent, and the levulinic acid from the second reactor to a separator; and separating the levulinic acid from the mineral acid and the solvent in the separator.

20. The method of claim 19, wherein the biomass feed is contacted with the mineral acid to produce the partially hydrolyzed biomass in the first reactor, and wherein the mineral acid is present in the first reactor in an amount of up to 10% by weight of the biomass feed.

* * * * *